United States Patent [19]

Kimura et al.

[11] Patent Number: 5,618,564
[45] Date of Patent: Apr. 8, 1997

[54] COMPOSITION FOR THE TREATMENT OF HELICOBACTER PYLORI INFECTION

[75] Inventors: Ken Kimura, 31-3 Shimouma 1-chome, Setagaya-ku, Tokyo 154, Japan; Yushi Taniguchi; Kiichi Satoh, both of Oyama, Japan; Kouji Saifuku, Shimodate, Japan; Ken Kihira, Kawachi, Japan; Kenichi Ido, Utsunomiya, Japan; Yukio Yoshida, Urawa, Japan; Takuya Takimoto, Kawachi, Japan

[73] Assignees: Ken Kimura; Kaken Pharmaceutical Co., Ltd., both of Japan

[21] Appl. No.: 508,321

[22] Filed: Jul. 27, 1995

[30] Foreign Application Priority Data

Jun. 14, 1995 [JP] Japan ................................... 7-147701

[51] Int. Cl.⁶ .......................... A61K 33/24; A61K 38/00; A61K 31/65; A61K 31/43; A61K 31/415; A61K 31/29

[52] U.S. Cl. ............................ 424/653; 514/2; 514/154; 514/199; 514/398; 514/503; 514/925; 514/926; 514/927

[58] Field of Search ................................. 424/653; 514/2, 514/154, 199, 398, 503, 925, 926, 927

[56] References Cited

U.S. PATENT DOCUMENTS

| | | | |
|---|---|---|---|
| 4,122,158 | 10/1978 | Schmitt | 424/27 |
| 4,153,685 | 5/1979 | Serfontein | 424/94 |
| 4,470,372 | 9/1984 | Boncic | 424/94.64 |
| 4,673,637 | 6/1987 | Hyman | 435/34 |
| 4,849,227 | 7/1989 | Cho | 424/498 |
| 4,906,670 | 3/1990 | Higashi et al. | 514/773 |
| 5,196,205 | 3/1993 | Borody | 424/653 |
| 5,229,380 | 7/1993 | Harris | 514/152 |
| 5,407,688 | 4/1995 | Place | 424/653 |

OTHER PUBLICATIONS

Chem. Abstract 74:130384, Serfontein, "Therapeutic Bismuth Preparations". Date 1970.
"The American Journal of Gastroenterology", vol 89, No. 8, Aug. 1994.
The American Journal of Gastroenterology Jan. 1995 vol. 90 No. 1, pp. 60–63 Kimura et al "A 1–h Topical Therapy for the Treatment of Helicobacter pylori Infection".
The First Meeting of the Japanese Research Society for Helicobacter Pylori Related Gastroduodenal Diseases Apr. 1, 1995.

*Primary Examiner*—Raymond Henley, III
*Attorney, Agent, or Firm*—Nixon & Vanderhye

[57] ABSTRACT

The present invention is directed to a method for the treatment of *Helicobacter pylori* infection wherein a composition containing protease and an antibacterial agent as active ingredients, which can remove *Helicobacter pylori* from a stomach at high probability without causing side effects or the occurrence of resistant bacteria, and which can treat and prevent peptic ulcer caused by *Helicobacter pylori* infection and can prevent the recurrence of peptic ulcer is employed.

12 Claims, No Drawings

COMPOSITION FOR THE TREATMENT OF HELICOBACTER PYLORI INFECTION

FIELD OF THE INVENTION

The present invention relates to a composition for the treatment of the infection by bacteria *Helicobacter pylori* which is one of causes for gastric ulcer, duodenal ulcer, and the like.

PRIOR ART OF THE INVENTION

It has been so far thought that peptic uclers such as gastric ulcer, duodenal ulcer, and the like occur as a result of the failure in a balance between the attack destruction of a visceral wall by digestive liquids and the protection restoration thereof. For the therapy of peptic ulcers, therefore, attack factor inhibitors (e.g., a stomach acids neutralizer, a stomach acids secretion inhibitor, etc.) or protective-factor promoters (e.g., mucosa protecter, etc.) have been and are used.

It is well known that there are many peptic ulcers which recur if the administration of the above therapeutical preparations is discontinued even after the peptic ulcers are once cured. As one of causes of the recurrence, the infection by endogastric *Helicobacter pylori* has been reported. *Helicobacter pylori* (to be abbreviated as *H. pylori*" hereinafter) which is classified as one included in the spiral hyphae inhabiting gastric mucosal epithelium is attracting attention as bacterium which causes chronic gastritis and peptic ulcer. Concerning the relation between gastric mucosa lesion and *H. pylori*, in particular, it has been considered that *H. pylori* is highly involved in the manifestation thereof since *H. pylori* is specifically found in the pyloritic-vestibular part of stomach.

It is also reported that if infected *H. pylori* is eliminated, gastric ulcer is completely cured and that its recurrence is no longer observed.

As therapeutical preparations for the treatment of *H. pylori* infection, various chemicals as shown in the following Table 1 are used at present.

TABLE 1

| | Chemicals | Bacteria removal ratio* |
|---|---|---|
| Group of administration of single chemical | CBS, BSS, AMPC, cefixime, tinidazole, thiamphenicol, doxycycline | 18.6% (98/527) |
| Group of administration of two chemicals | CBS + AMPC, BSS + AMPC, CBS + metronidazole, BSS + metronidazole, AMPC + metronidazole, AMPC + tinidazole, AMPC + OFLX, CBS + tinidazole, BSS + EM, thiamphenicol + AMPC, BSS + nitrofurantoin, CBS + tinidazole | 48.2% (265/550) |
| Group of administration of three chemicals | CBS + metronidazole + AMPC, BSS + metronidazole + AMPC, CBS + metronidazole + TC, BSS + metronidazole + TC, furazolidone + metronidazole + AMPC, BSS + metronidazole + penicillin | 82.3% (320/389) |

Notes)
CBS: colloidal bismuth,
BSS: bismuth subsalicylate
AMPC: amoxicillin
OFLX: ofloxacin
EM: erythromycin
TC: tetracycline

*) Bacteria removal ratio (%) = $\dfrac{\text{Number of patients succeeded in the removal of } H.\ pylori}{\text{Number of all patients treated with the chemicals}} \times 100$ As is clear in the above Table 1, the bacterial removal ratio against *H. pylori* is 18.6% when a single chemical is administered, 42.8% when a two-component preparation is administered, or 82.3% when a three-component preparation is administered. It is a dominant mainstream at present to employ the method using the administration of three chemicals.

Under the above circumstances, for the treatment of *H. pylori* infection, there are used antibiotics such as penicillins, tetracyclines and macrolides, and new quinolone type antibaceterial agents, while their efficacy of bacteria removal is not satisfactory. It is considered not only because *H. pylori* has the nature of easily altering to one resistant to an antibacetrial agent but also because no sufficient amount of chemicals reach a topical infection site due to the barrier of a mucosal layer that many antibacterial substances fail to completely remove *H. pylori* out of the stomach.

A gastric mucosal epithelium is covered with a hydrophobic mucosal layer having a large thickness, and it is therefore difficult for a large amount of a hydrophilic compound having a low molecular weight such as antibacterial agents to infiltrate the mucosa, reach the mucosal topical site where *H. pylori* inhibits and proliferates, and remain for a predetermined period of time. Further, it is in numerous gastric pits present in the gastric mucosal epithelium that *H. pylori* proliferates, and there is a difficulty of an antibaceterial agent reaching *H. pylori*.

In the presently dominant therapy using plurality of chemicals in combination, the baceteria removal ratio improves to a considerable extent, while side effects are highly frequently observed and the administration method is complicated, so that there is a defect in that the reliable administration is difficult.

SUMMARY OF THE INVENTION

It is an object of the present invention to provide a composition and a method for the treatment of *H. pylori* infection, which accomplishes a more reliable and safe effect on the treatment of *H. pylori* infection in a short period of time.

It is another object of the present invention to provide a preparation containing the above composition and a method, for the prevention, therapy, and prevention of recurrence of peptic ulcer and chronic gastritis.

According to the present invention, the above objects and advantages of the present invention are achieved by a composition for the treatment of *H. pylori* infection, containing a protease and an antibacterial agent as active ingredients, and a preparation containing the composition, for the prevention, therapy and prevention of recurrence peptic ulcer and chronic ulcer caused by the *H. pylori* infection.

Further, by using the composition of the present invention under a specific topical therapy, the excellent bacteria-removing effect can be obtained.

DETAILED DESCRIPTION OF THE INVENTION

For achieving the above objects, the present inventors have made diligent studies, and have found that a pharmaceutical composition containing a combination of a specific protease with a conventional antibacterial agent can remove *H. pylori* at a high probability, and on the basis of this finding, the present invention has been completed.

First, the protease, one of the active ingredients in the composition for the treatment of *H. pylori* infection, provided by the present invention, will be explained below.

The protease is not specially limited if it has the activity of decreasing the viscosity of mucin of gastric mucosal epithelium. Examples of the protease used in the present invention include pronase, trypsin, α-chymotorypsin, serrapeptase, bromelain and pepsin. Preferred protease is pronase.

The activity of pronase decreasing the viscosity of mucin which is a viscous substance is remarkably high as compared with those of other proteases such as trypsin, α-chymotrypsin, serrapeptase, bromelain and pepsin. The optimal pH for the activity of decreasing the viscosity of 2% mucin is 7 to 10.

Pronase is a protease having a molecular weight of approximately 20,000 to 30,000, produced by Actinomyces, *Streptomyces griceus*. As properties, it is a powder having a white to brownish color, has a specific odor, and tastes bitter to a slight extent. It is easily soluble in water, but is hardly soluble in ethanol and diethyl ether. A solution of 1 g of pronase in 100 ml of water shows a pH of 6.7 to 8.3.

As physiological activities of pronase, there are known the proteolytic activity (in vitro, high decomposition activity by acting on almost all peptide bonds), the activity of decomposing phlogogenic polypeptide (in vitro, decomposition power over bradykinin which is phlogogenic polypeptide, to inhibit the activity of the same), the activity of fusing a viscous substance (in human and in vitro, the activity of decomposing mucin, to decrease the viscosity of expectoration and purulent matter), the activity of fibrinolysis (in vitro, the activity of dissolving fibrin formed and accumulated in inflammatory focus), the anti-inflammatory and anti-swelling activity and the activity of promoting the transition of an antibiotic to a focal site.

On the basis of the above physiological activities, pronase is clinically widely used for the alleviation of the swelling after a surgical operation and after injury, for the alleviation of the swelling of sinusitis and for the promotion of expectoration in bronchitis, bronchial asthma and pulmonary tuberculosis.

The present inventors have expected that *H. pylori* can be effectively removed in a short period of time by fusing gastric mucosa protecting *H. pylori*, with a protease and exposing the *H. pylori* inhabiting gastric mucosal epithelium directly to an antibacterial agent, and have studied and tested various proteases. As a result, the present inventors have come to a conclusion that the above pronase exhibits the remarkably high activity of fusing a viscous substance than any other protease, has a high effect on the removal of *H. pylori* and is the most suitable for achieving the objects of the present invention.

The antibacterial agent used as other active ingredient in the composition for the treatment of *H. pylori* infection, provided by the present invention, will be explained hereinafter.

The antibacterial agent is not specially limited if it has the activity of inhibiting the proliferation of *H. pylori* or killing *H. pylori*. Generally, it is selected from antibiotics, anti-protozoan drugs, bismuth preparations, etc. The antibacterial agents may be used alone or in combination. Generally, the administration of a combination of at least two antibacterial agents shows a higher efficacy of *H. pylori* removed.

Examples of the antibiotics used as one antibacterial agent in the present invention include penicillins such as amoxicillin and ampicillin; cephems such as cefaclor, cephalothin, cefotaxime; macrolides lincomycins such as erythromycin, clarithromycin, josamycin, lincomycin and clindamycin; tetracyclines such as tetracycline and minocycline; synthetic antibacterial drugs such as ofloxacin, norfloxacin and ciprofloxacin; and others such as fosfomycin, imipenem and latamoxef. Of these, amoxicillin out of the penicillins and clarithromycin out of the macrolides are preferred since they exhibit excellent antibacterial activities.

Examples of the anti-protozoan drugs used as one antibacterial agent in the present invention include metronidazole and tinidazole, and metronidazole is preferred.

Examples of the bismuth preparations used as one antibacterial agent in the present invention include bismuth, bismuth subnitrate, bismuth subsalicylate and colloidal bismuth. Bismuth subnitrate is preferred.

In the antibacterial agent as one of active ingredients in the composition for the treatment of *H. pylori* infection, provided by the present invention, for example, the combination of bismuth subnitrate (bismuth preparation), amoxicillin (antibiotic) and metronidazole (anti-protozoan drug) is particularly preferred since the combination exhibits an excellent bacetria-removing effect.

In addition to protease and the antibacterial agent, the composition for the treatment of *H. pylori* infection, provided by the present invention, may contain a drug which does not any antibacterial activity against *H. pylori* when used alone. This drug includes drugs which protect a stomach wall which may be injured by procedures of the treatment of *H. pylori* infection, and drugs which prevent the secretion of stomach acids, such as a proton pump inhibitor, an $H_2$ receptor antagonist and a mucosa protective-factor enhancer.

Examples of the proton pump inhibitor include from benzimidazole-containing compounds such as omeprazole and lansoprazole, and omeprazole and lansoprazole are preferred.

Examples of the $H_2$ receptor antagonist include cimetidine, ranitidine and famotidine.

Examples of the mucosa protective-factor enhancer include sofalcone and plaunotol.

Preferred examples of preparations of the composition for the treatment of *H. pylori* infection, provided by the present invention, will be explained hereinafter.

The composition for the treatment of *H. pylori* infection, provided by the present invention, can be administered in the form of a solution or a powder, while a solution is preferred. The solution may be prepared by dissolving or suspending protease and the antibacterial agent in a bicarbonate aqueous solution or the like. Generally used auxiliaries such as physiological saline, glucose, sucrose, gelatin, a buffer solution, and the like may be added as required.

When the composition for the treatment of *H. pylori* infection, provided by the present invention, is a solution, the amount of the solution is generally 100 to 200 ml, although the amount depends upon kind and symptoms of a disease, the height, weight, age and health condition of a patient.

When the composition for the treatment of *H. pylori* infection, provided by the present invention, is a solution, the amount of pronase is 0.02 to 0.1% by weight. Therefore, the amount of pronase in the solution having the above concentration is 20,000 to 100,000 tyrosine units.

The amount of the antibacterial agent is 3 to 10% by weight in a total. When the antibacterial agent is the above combination particularly preferred, the amount of bismuth subnitrate is 1 to 4% by weight, the amount of amoxicillin is 1 to 4% by weight and the amount of metronidazole is 1 to 2% by weight.

The amount of other optional pharmaceutical component is to be determined depending upon the object of use, its kind, the kind of a disease, the age, physique and health condition of a patent, etc.

The method of administering the composition for the treatment of *H. pylori* infection, provided by the present invention, is preferably a topical administration. In the specific treatment of *H. pylori* infection, the composition for the treatment of *H. pylori* infection, provided by the present invention, is directly instilled into a stomach such that the composition is brought into contact with the whole of gastric mucosa without contacting the composition with the esophageal wall or the like. When the composition for the treatment of *H. pylori* infection is instilled into a stomach of a patient, an intestinal tube or a bouble lumen tube with a balloon is inserted into a second portion of the duodenum, the balloon at its tip was inlfated to block the superior duodenal angulus (postbulbary) part of the stomach so that the composition is prevented from leaking from the stomach to a small intestine. The composition for the treatment of *H. pylori* infection is directly instilled into the stomach through the intestinal tube or the like. After the composition is instilled into the stomach, the patient's position is changed at predetermined intervals (generally every 15 minutes) such that the composition is brought into contact with the whole of the gastric wall. The treatment of *H. pylori* infection with the composition finishes generally in about from 1 to 2 hours. After the treatment is finished, gastric contents including the composition are suctioned out of the patient with the intestinal tube, or the like.

By the above treatment, the concentration of the active ingredients of the composition for the treatment of *H. pylori* infection can be maintained at a high level, and a high effect of removing *H. pylori* can be accomplished in a short period of time.

Prior to the administration of the composition of the present invention, a protease and a proton pump inhibitor such as lansoprazole may be administered. It is assumed that the prior atministration of the protease reduces the amount of gastric mucus to produce an effect of preventing a decrease in the concentration of the composition of the present invention. It is also assumed that the prior administration of the proton pump inhibitor inhibits the secretion of acids to produce an effect of enhancing the antibacterial activity of the antibiotic included in the antibacterial agent as one of the active ingredient of the composition of the present invention.

As explained above, the composition for the treatment of *H. pylori* infection, provided by the present invention, is useful as a drug for the prevention and therapy of peptic ulcer or chronic gastritis caused by *H. pylori* infection, and further, is useful as a drug for the prevention of its recurrence.

EXAMPLES

The present invention will be explained more in detail with reference to Examples hereinafter.

EXAMPLE 1

Patients: 25 patients (16 men and 9 women), age 24–79, infected with *H. pylori* in the stomach.

Method of administration of drug: The patients were administered with 30 mg of lansoprazole (proton pump inhibitor) before they went to bend for the night, and with 18,000 tyrosine units of pronase twice a day, for 2 days. Then, an intestinal tube was inserted into the second portion of the duodenum in each patient, and a balloon was inflated postbulbarly to prevent the leakage of a composition (solution) for the treatment of *H. pylori* infection, provided by the present invention, which was to be instilled into the stomach. Then, a composition of the present invention, which was a suspension of 1 g of bismuth subnitrate, 2 g of amoxicillin, 1 g of metronidazole and 36,000 tyrosine units of pronase in 100 ml of a 7% bicarbonate aqueous solution, was instilled into the stomach of each patient through the tube, and the patients' positions were changed every 15 minutes (from the sitting to the supine, prone, and right lateral position) to bring the composition into contact with the whole of gastric mucosa. One hour after the administration of the composition, gastric contents containing the composition were recovered.

Results: The treatment of *H. pylori* infection with the composition of the present invention succeeded in the removal of *H. pylori* in 24 patients out of the 25 patients (bacteria removal ratio 96%). Further, in one patient for whom the treatment failed in the removal of *H. pylori*, it was found that the composition had leaked into the small intestine since the blockade at the superior duodenal angulus part with the balloon had been incomplete. In this one patient, therefore, slight loose-stools were observed as a side effect. In the 24 patients for whom the treatment succeeded in the removal of *H. pylori*, no side effects were observed, the recovery was smooth, and no recurrence of peptic ulcer was observed thereafter.

EXAMPLE 2

Patients: 18 patients, infected with *H. pylori* in the stomach

Method of administration of drug: The patients were administered with 30 mg of lansoprazole (proton pump inhibitor) before they went to bend for the night, and with 18,000 tyrosine units of pronase twice a day, for 2 days. Then, a bouble lumen tube with a balloon was inserted into the second portion of the duodenum in each patient, and the balloon was inflated postbulbarly to prevent the leakage of a composition (solution) for the treatment of *H. pylori* infection, provided by the present invention, which was to be instilled into the stomach. Then, a composition of the present invention, which was a suspension of 4 g of bismuth subnitrate, 4 g of amoxicillin, 1 g of metronidazole and 36,000 tyrosine units of pronase in 100 ml of a 7% bicarbonate aqueous solution, was instilled into the stomach of each patient through the tube, and maintained for 2 hours. After the instillation of the composition of the present invention, the patients' positions were changed every 30 minutes to bring the composition into contact with the whole of gastric mucosa. Two hours after the administration of the composition, gastric contents containing the composition were recovered.

Results: The treatment of *H. pylori* infection with the composition of the present invention succeeded in the removal of *H. pylori* in 15 patients out of the 18 patients (bacteria removal ratio 83.3%). In the 15 patients for whom the treatment had succeeded in the removal of *H. pylori*, the presence of *H. pylori* was not found in the tests (smear test, culturing, histological test and biopsy) which were conducted 4 weeks after the treatment, nor were side effects observed. Further, a side effect was observed in one case alone in which the composition had leaked into the small intestine since the blockade at the superior duodenal angulus part with the balloon had been incomplete. The patients for whom the treatment had succeeded in the removal of *H. pylori* recovered smoothly and showed no recurrence of peptic ulcer thereafter.

EXAMPLE 3

Patients: 28 patients, infected with *H. pylori* in the stomach

Method of administration of drug: The patients were administered with 30 mg of lansoprazole (proton pump inhibitor) before they went to bend for the night, and with 18,000 tyrosine units of pronase twice a day, for 2 days. Then, a bouble lumen tube with a balloon was inserted into the second portion of the duodenum in each patient, and the balloon was inflated postbulbarly to prevent the leakage of a composition (solution) for the treatment of *H. pylori* infection, provided by the present invention, which was to be instilled into the stomach. Then, a composition of the present invention, which was a suspension of 4 g of bismuth subnitrate, 4 g of amoxicillin, 2 g of metronidazole and 36,000 tyrosine units of pronase in 100 ml of a 7% bicarbonate aqueous solution, was instilled into the stomach of each patient through the tube, and maintained for 2 hours. After the instillation of the composition of the present invention, the patients' positions were changed every 30 minutes to bring the composition into contact with the whole of gastric mucosa. Two hours after the administration of the composition, gastric contents containing the composition were recovered.

Results: The treatment of *H. pylori* infection with the composition of the present invention succeeded in the removal of *H. pylori* in 23 patients out of the 28 patients (bacteria removal ratio 82.1%). In the 23 patients for whom the treatment had succeeded in the removal of *H. pylori*, the presence of *H. pylori* was not found in the tests (smear test, culturing, histological test and biopsy) which were conducted 4 weeks after the treatment, nor were side effects observed. Further, a side effect was observed in one case alone in which the composition had leaked into the small intestine since the blockade at the superior duodenal angulus part with the balloon had been incomplete. The patients for whom the treatment had succeeded in the removal of *H. pylori* recovered smoothly and showed no recurrence of peptic ulcer thereafter.

In the group of administration of three chemicals using no pronase, shown in Table 1, the bacteria removal ratio is 82.3%, which appears to be equivalent to the above bacteria removal ratios accomplished by the compositions of the present invention in Examples 2 and 3. When no pronase is used, however, it is difficult to remove bacteria in a short period of time unlike the treatment in the present invention. Further, there is another problem in that various side effects induced by chemicals are observed. Therefore, the efficacy of the present invention shall not be evaluated on the basis of the bacteria-removal success ratio alone.

The present invention provides a composition and a method for the treatment of *H. pylori* infection, which can remove the intected *H. pylori* in the stomach, for which no effective therapeutical method has been established so far, at high probability. According to the composition for the treatment of *H. pylori* infection, provided by the present invention, *H. pylori* in the stomach can be reliably removed, and almost no side effects occur. Further, *H. pylori* can be removed by the treatment in a short period of time so that the mental and physical burden on patients can be decreased. Further, the period of time for which the antibacterial agent is in contact with *H. pylori* is short, so that the occurrence of bacteria resistant to the antibacterial agent can be prevented.

The composition for the treatment of *H. pylori* infection is useful for the therapy and prevention of peptic ulcer and chronic ulcer caused by the *H. pylori* infection, and is further useful for the prevention of the recurrence of these diseases.

What is claimed is:

1. A method for the therapy of a *Helicobacter pylori* infected patient, which comprises blocking a part of the patient's superior duodenal angulus to prevent gastric contents from leaking into the small intestine, then directly instilling a composition which contains, as active ingredients, a protease and an antibacterial agent into the patient's stomach thereby treating the gastric wall through exposure of said wall to said composition for a predetermined period of time in which the position of the patient is changed, and recovering the gastric contents from the patient's stomach after the treatment.

2. The method of claim 1, wherein the protease is selected from the group consisting of pronase, trypsin, α-chymotrypsin, serrapeptase, bromelain and pepsin.

3. The method of claim 2, wherein the protease is pronase.

4. The method of claim 3, wherein the amount of pronase is 0.02 to 0.1% by weight.

5. The method of claim 1, wherein the amount of antibacterial agent is 3 to 10% by weight in a total.

6. The method of claim 1, wherein the antibacterial agent is selected from the group consisting of an antibiotic, an anti-protozoan drug and a bismuth preparation.

7. The method of claim 6, wherein the antibiotic is selected from the group consisting of amoxicillin, erythromycin and clindamycin.

8. The method of claim 6, wherein the anti-protozoan drug is selected from the group consisting of metronidazole and tinidazole.

9. The method of claim 6, wherein the bismuth preparation is selected from the group consisting of bismuth, bismuth subnitrate, bismuth subsalicylate and colloidal bismuth.

10. The method of claim 6, wherein the composition comprises as the antibacterial agents amoxicillin, metronidazole and bismuth subnitrate.

11. The method of claim 10, wherein the amount of bismuth subnitrate is 1 to 4% by weight, the amount of amoxicillin is 1 to 4% by weight and the amount of metronidazole is 1 to 2% by weight.

12. The method of claim 1, wherein the composition is a solution.

\* \* \* \* \*